(12) United States Patent
Yamanouchi et al.

(10) Patent No.: US 8,748,410 B2
(45) Date of Patent: Jun. 10, 2014

(54) METHODS OF TREATING ANEURYSM

(75) Inventors: Dai Yamanouchi, Madison, WI (US); K. Craig Kent, Fitchburg, WI (US); Bo Liu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/229,093

(22) Filed: Sep. 9, 2011

(65) Prior Publication Data

US 2012/0064088 A1 Mar. 15, 2012

Related U.S. Application Data

(60) Provisional application No. 61/381,271, filed on Sep. 9, 2010.

(51) Int. Cl.
*A61K 31/663* (2006.01)
*A61K 39/395* (2006.01)
*A61P 9/00* (2006.01)
*A61K 31/675* (2006.01)

(52) U.S. Cl.
USPC .......... 514/107; 424/158.1; 514/108; 514/89; 514/94; 514/102; 548/414; 562/21

(58) Field of Classification Search
USPC .......... 514/107, 108, 102, 89, 94; 424/158.1; 548/414; 562/21
See application file for complete search history.

(56) References Cited

U.S. PATENT DOCUMENTS

2006/0069068 A1 3/2006 Kajander et al.

FOREIGN PATENT DOCUMENTS

WO  WO 0149295  * 7/2001  ............ A61K 31/66

OTHER PUBLICATIONS

Jayalath et al. (Eur. J. Vasc. Endovasc. Surg., 30, 2005, pp. 476-488.*
Meddean.luc AAA document (Abdominal Aortic Aneurysm (AAA), 2006, pp. 1-6, retrieved from the internet on Jun. 27, 2012 and URL: http://www.meddean.luc.edu/lumen/meded/Radio/curriculum/Surgery/Aneurysm1.htm.*
Hamerman, D. "Osteoporosis and atherosclerosis: biological linkages and the emergence of dual-purpose therapies" 2005 Q J Med 98:467-484.
Price, P.A. et al., "Bisphosphonates Alendronate and Ibandronate Inhibit Artery Calcification at Doses Comparable to Those That Inhibit Bone Resorption" 2001 Arterioscler Thromb Vasc Biol 21; 817-824.
Doherty, T.M. et al., "Calcification in atherosclerosis: Bone biology and chronic inflammation at the arterial crossroads" 2003 PNAS vol. 100 No. 20 pp. 11201-11206.
Nordon I.M, et al., "Review of Current Theories for Abdominal Aortic Aneurysm Pathogenesis" 2009 Vascular vol. 17 No. 5 pp. 253-263.
Kuehn, B. M., "Studies Probe Possible Link Between Bisphosphonates and Femoral Fractures" 2010 JAMA 303 (18):1795-1796.
Abrahamsen, B. et al., "Subtrochanteric and Diaphyseal Femur Fractures in Patients Treated With Alendronate: A Register-Based National Cohort Study" 2009 Journal of Bone and Mineral Research vol. 24 No. 6 pp. 1095-1102.

* cited by examiner

*Primary Examiner* — Savitha Rao
(74) *Attorney, Agent, or Firm* — Quarles & Brady LLP

(57) ABSTRACT

The present invention is directed to a method for treating aneurysms in vascular tissue. The method includes administering a bisphosphonate compound to a subject in an amount which is effective against the formation or progression of aneurysm, or which is effective to induce regression of an established aneurysm. In alternative methods, an anti-RANKL neutralizing antibody is administered to the subject to achieve analogous anti-aneurysm effect. The methods of particular advantage in the treatment of subjects having an abdominal aortic aneurysm, a relatively common, and life-threatening, condition.

21 Claims, 4 Drawing Sheets

METHODS OF TREATING ANEURYSM

CROSS-REFERENCE TO RELATED APPLICATION

This application claims the benefit of U.S. Provisional Application 61/381,271, filed Sep. 9, 2010, which is incorporated herein by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to methods for treating and preventing aneurysm in vascular tissue. More particularly, the present invention relates to the treatment and prevention of aneurysm, preferably abdominal aortic aneurysm, by the administration of bisphosphonate compounds or certain antibodies.

BACKGROUND OF THE INVENTION

Aortic aneurysms are weakened/bulging areas in the aorta, the largest blood vessel in the body. Abdominal aortic aneurysms ("AAAs") are significantly more common in men, and are the 10th leading cause of death in men over age 55. In fact, annual deaths from ruptured AAAs may be as high as 30,000, which is comparable to the number of annual deaths from prostate cancer or breast cancer.

Abdominal aortic aneurysms are generally identified through screening of patients with specific health histories that suggest that they may be candidates for aneurysms. Studies have found that mortality can be reduced for patients with large aneurysms through surgical intervention. However, for small aneurysms, such intervention has not proven to improve survival rates, so such patients are monitored but remain untreated.

Arterial calcification, such as that which occurs in atherosclerosis (i.e. hardening of the arteries), has been reported to be associated with a high risk of adverse clinical events. Recent studies have suggested that the calcification of arteries is an organized and regulated process with many similarities to bone mineralization. The mineralization of bone is controlled by a balance of the actions of osteoblast cells (which deposit minerals such as calcium) and osteoclast cells (which resorb minerals and decalcify bone). Similarly, the calcification of arterial plaques in subjects with atherosclerosis is hypothesized to be controlled by osteoblast-like cells and osteoclast-like cells. However, the mechanism is not understood, and studies have, paradoxically, shown that patients that have osteoporosis, in which excessive osteoclast activity causes bone demineralization (out of balance with osteoblast activity), also have high arterial calcification (too much mineralization of the arteries). Similarly, studies have suggested that treating subjects with bisphosphonates, a class of osteoporosis drug that inhibits osteoclasts, has the dual benefit of improving bone density and reducing arterial calcification.

Since aneurysms result from the weakening, rather than the hardening, of arteries, it is not yet clear whether calcification is physiologically relevant to the formation and progression of aneurysms. Though it was once assumed that aneurysms occurred as a consequence of advanced atherosclerosis, increasing evidence suggests that they may be distinct (if somewhat related) phenomena that share a few, but not all, clinical risk factors.

At present, aneurysms are treated by either endovascular techniques (endovascular stent graft) or open surgery techniques. Open techniques include bypass surgery with a prosthetic graft and excision. Bypass surgery of an aneurysm means placing the prosthetic graft to cut off blood flow through the aneurysm. If the aneurysm is infected or mycotic, it may then be excised (cut out and removed from the body). If uninfected, the aneurysm is often left in place.

For aneurysms in the aorta, arms, legs, or head, the weakened section of the vessel may be replaced by a bypass graft that is sutured at the vascular stumps. Instead of sewing, the graft tube ends, made rigid and expandable by nitinol wireframe, can be inserted into the vascular stumps and permanently fixed there by external ligature. New devices were recently developed to substitute the external ligature by expandable ring allowing use in acute ascending aorta dissection, providing airtight, easy and quick anastomosis extended to the arch concavity. Less invasive endovascular techniques allow covered metallic stent grafts to be inserted through the arteries of the leg and deployed across the aneurysm.

As can be appreciated from the above discussion, a need exists for improved clinical therapies to prevent and/or treat aneurysms. Accordingly, it is one of the purposes of the present invention to treat vascular and especially abdominal aortic aneurysms, by providing a method of preventing their formation, but without being subject to undesirable side effects or requiring intrusive or invasive interventions. It is another purpose of the invention to provide a method of inducing the regression of established aneurysms to cause the vessel to return to a safer and relatively more normal state.

SUMMARY OF THE INVENTION

In a first aspect, the present invention provides a method for treating an aneurysm in the vascular tissue of a subject. Such a method includes administering an anti-aneurysmal amount of a bisphosphonate compound to a subject in need of anti-aneurysmal therapy, thereby inhibiting the development of, or inducing the regression of, an aneurysm in the vascular tissue of the subject. The vascular tissue to be treated is preferably an artery of the subject, more preferably an abdominal aorta of the subject.

Administration of the bisphosphonate compound to the subject is, in certain embodiments, carried out by intravenous injection, or, alternatively, by oral administration of bisphosphonate compound to the subject.

A wide variety of bisphosphonate compounds are useful in the present method including, for example, etidronate, clodronate, tiludronate, pamidronate, neridronate, olpadronate, alendronate, ibandronate, risedronate, zoledronate, or a mixture thereof.

In particular embodiments, the bisphosphonate is selected from non-nitrogen-containing bisphosphonate, and, in yet other methods, the bisphosphonate is a nitrogen-containing bisphosphonate. A preferred nitrogen-containing bisphosphonate is pamidronate, and a preferred non-nitrogen-containing bisphosphonate is etidronate.

In yet another aspect, the invention is directed to a method for inhibiting development of, or inducing regression of, an aneurysm in vascular tissue susceptible to the formation of, or exhibiting, an aneurysm. Such a method includes contacting the vascular tissue with a bisphosphonate compound in an amount sufficient to inhibit development of, or induce regression of, an aneurysm in the vascular tissue.

A wide variety of bisphosphonate compounds are useful in this method including, for example, etidronate, clodronate, tiludronate, pamidronate, neridronate, olpadronate, alendronate, ibandronate, risedronate, zoledronate, or a mixture thereof In particular embodiments, the bisphosphonate is selected from non-nitrogen-containing bisphosphonate, and, in yet other methods, the bisphosphonate is a nitrogen-containing bisphosphonate. A preferred nitrogen-containing bisphosphonate is pamidronate, and a preferred non-nitrogen-containing bisphosphonate is etidronate.

The vascular tissue is, in certain embodiments, arterial tissue, preferably of the aortic variety, more preferably of the abdominal aortic variety. Depending on the specific method, the bisphosphonate compound may be contacted with the vascular tissue in situ (e.g., by injection at the tissue's site a subject) or, alternatively, ex vivo (e.g., by surgical removal of the tissue and bisphosphonate contact outside of the subject's body, followed by surgical replacement of the tissue).

In another aspect, the invention provides a method for treating an aneurysm in vascular tissue of a subject which includes the step of administering an anti-aneurysmal amount of an anti-RANKL neutralizing antibody to a subject in need of anti-aneurysmal therapy, thereby inhibiting the development of, or inducing the regression of, an aneurysm in the vascular tissue of the subject.

The vascular tissue is preferably an artery of the subject, more preferably the aorta of the subject, namely the subject's abdominal aorta. Administration of the anti-RANKL neutralizing antibody is, e.g., via subcutaneous injection of the antibody to the subject.

In another aspect, the invention encompasses a method for inhibiting development of, or inducing regression of, an aneurysm in vascular tissue susceptible to the formation of, or exhibiting, an aneurysm. Such a method includes the step of contacting the vascular tissue with an anti-RANKL neutralizing antibody in an amount sufficient to inhibit development of, or induce regression of, an aneurysm in the vascular tissue.

The invention further encompasses methods of formulating/manufacturing pharmaceutical compositions (alternatively termed "medicaments") for the treatment of aneurysm, preferably abdominal aortic aneurysm, in a subject as well as bisphosphonate compounds or anti-RANKL neutralizing antibodies for use in treating aneurysm in vascular tissue of a subject.

This invention provides the advantage over prior technologies in that embodiments of the invention utilize or are based on the administration of bisphosphonate compounds or anti-RANKL neutralizing antibodies which are, in large part, widely known and well regarded for treatment of unrelated diseases/disorders.

Other objects, features and advantages of the present invention will become apparent after review of the specification, claims and drawings. The detailed description and examples enhance the understanding of the invention, but are not intended to limit the scope of the appended claims.

DETAILED DESCRIPTION OF THE INVENTION

I. In General

Figure 1:
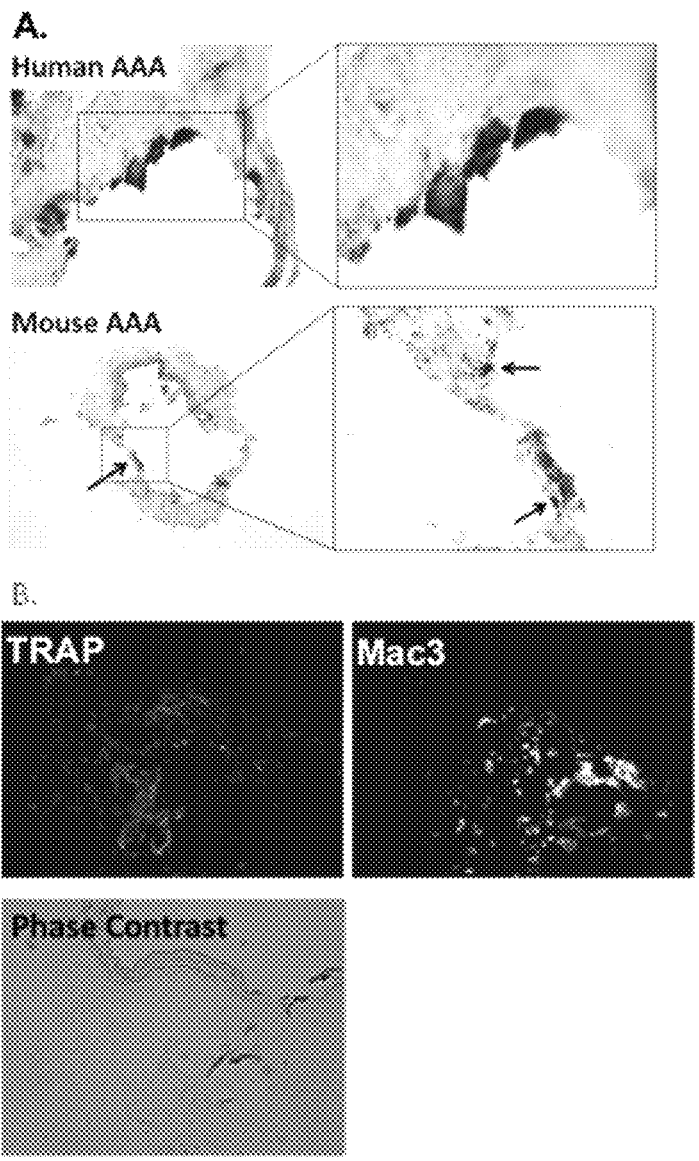
FIG. 1 depicts osteoclasts ("OLCs") in AAA. (A) Representative pictures of TRAP staining of human AAA and $CaCl_2$ AAA. (B) Immunofluorescence staining of mouse AAA stained for anti-TRAP, Macrophage (Mac3) and phase contrast as a reference.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of medicinal chemistry, pharmacology, organic chemistry, analytical chemistry, molecular biology, microbiology, and immunology, which are within the skill of the art. Such techniques are explained fully in the literature.

As used herein, the term "subject" refers to an animal, preferably a mammal, even more preferably a human. The terms "patient" and "subject" are used interchangeably herein. The conditions treatable by means of the present invention occur primarily in mammalian subjects. Human patients are by far the most important subjects treatable according to the method of the invention, but the method can be practiced for the benefit of other mammals, including, for example, pet animals such as dogs and cats, laboratory animals such as rats and mice, as well as farm animals such as horses and cows.

"Therapeutically effective amount" means the amount of a compound that, when administered to a subject for treating a disease or disorder, is sufficient to effect such treatment for the disease or disorder. The "therapeutically effective amount" can vary depending on the compound, the disease or disorder and its severity, and the age, weight, etc., of the subject to be treated.

"Treating" or "treatment" of any disease or disorder refers, in one embodiment, to ameliorating the disease or disorder (i.e., arresting or reducing the development of the disorder or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same (i.e., a prophylactic therapy).

As used herein, the term "aneurysm" refers to a localized, blood-filled dilation (balloon-like bulge) of a blood vessel caused by disease or weakening of the vessel wall. Aneurysms most commonly occur in arteries at the base of the brain (the circle of Willis) and in the aorta (the main artery coming out of the heart, an aortic aneurysm). As the size of an aneurysm increases, there is an increased risk of rupture, which can result in severe hemorrhage, other complications or even death. "Aneurysm" further means not only conventional vascular aneurysms, but also refers to any abnormal localized dilatations of blood vessels.

"Abdominal aortic aneurysm" (also known as "AAA", pronounced "triple-a") is a localized dilatation (ballooning) of the abdominal aorta exceeding the normal diameter by more than 50 percent. Approximately 90 percent of abdominal aortic aneurysms occur infrarenally (below the kidneys), but they can also occur pararenally (at the level of the kidneys) or suprarenally (above the kidneys). Such aneurysms can extend to include one or both of the iliac arteries in the pelvis. Abdominal aortic aneurysms occur most commonly in individuals between 65 and 75 years old and are more common among men and smokers. They tend to cause no symptoms, although occasionally they cause pain in the abdomen and back (due to pressure on surrounding tissues) or in the legs (due to disturbed blood flow). The major complication of abdominal aortic aneurysms is rupture, which can be life-threatening as large amounts of blood spill into the abdominal cavity, and can lead to death within minutes.

The term "bisphosphonate" (alternatively, "bisphosphonate compound") refers to a class of drugs that have previously been generally known to prevent the loss of bone mass, and commonly used to treat osteoporosis. These chemical entities are termed bisphosphonates because they have two phosphate ($PO_3$) groups and share a common P-C-P backbone. The two $PO_3$ (phosphonate) groups covalently linked to carbon determine both the name "bisphosphonate" and the function of the drugs. The general term "bisphosphonate", without further specifying, encompasses both non-N-containing bisphosphonates such as, e.g., etidronate (commercially available as DIDRONEL), clodronate (BONEFOS, LORON), and tiludronate (SKELID), and N-containing bisphosphonates including, e.g., pamidronate (APD, AREDIA), neridronate, olpadronate, alendronate (FOSAMAX), ibandronate (BONIVA), risedronate (ACTONEL), and zoledronate (ZOMETA, ACLASTA).

Receptor activator of nuclear factor kappa-B ligand (referred to herein as "RANKL"), also known as tumor necrosis factor ligand superfamily member 11 ("TNFSF11"), TNF-related activation-induced cytokine ("TRANCE"), osteoprotegerin ligand ("OPGL"), and osteoclast differentiation factor ("ODF"), is a protein that in humans is encoded by the TNFSF11 gene. RANKL is known to be important in bone metabolism. Further, this natural and necessary surface-bound molecule (also known as CD254) found on osteoblasts serves to activate osteoclasts, which are the cells involved in bone resorption. RANKL is a member of the tumor necrosis factor (TNF) cytokine family which is a ligand for osteoprotegerin. RANKL also has a function in the immune system, where it is expressed by T helper cells and is thought to be involved in dendritic cell maturation.

In general, a "neutralizing antibody" is an antibody which defends a cell from an antigen or infectious body by inhibiting or neutralizing any effect it has biologically. In the present invention, anti-RANKL neutralizing antibodies are used to treat aneurysms, particularly aortic aneurysms.

II. The Invention

Abdominal aortic aneurysm ("AAA") is usually diagnosed by physical exam, ultrasound, or computerized tomography ("CT"). Alternative less often used methods for visualization of an aneurysm include magnetic resonance imaging ("MRI") and angiography.

At present, the treatment options for asymptomatic AAA are conservative management, surveillance with a view to eventual repair, and immediate repair. There are currently two modes of repair available for an AAA: open aneurysm repair ("OR"), and endovascular aneurysm repair ("EVAR"). An intervention is often recommended if the aneurysm grows more than 1 cm per year or it is bigger than 5.5 cm. Repair is also indicated for symptomatic aneurysms.

Conservative management is indicated in patients where repair carries a high risk of mortality and in patients where repair is unlikely to improve life expectancy. The mainstay of the conservative treatment is smoking cessation. Surveillance is indicated in small asymptomatic aneurysms (less than 5.5 cm) where the risk of repair exceeds the risk of rupture. As an AAA grows in diameter the risk of rupture increases. Surveillance until the aneurysm has reached a diameter of 5.5 cm has not been shown to have a higher risk as compared to early intervention.

Surgery for an abdominal aortic aneurysm is known as AAA surgery or AAA repair. The threshold for repair varies slightly from individual to individual, depending on the balance of risks and benefits when considering repair versus ongoing surveillance. The size of an individual's native aorta may influence this, along with the presence of comorbidities that increase operative risk or decrease life expectancy.

Prior to the present invention, no effective drug therapy had been found to be useful to decrease the growth rate or rupture rate of AAAs. In fact, only a small number of studies have addressed this issue. There appears limited and preliminary evidence suggesting protective effects of drug therapy with angiotensin-converting enzyme inhibitors, beta-blockers, statins and doxycycline.

The present invention is based on using bisphosphonate compounds, which are already approved for osteoporosis indications, as a treatment for aneurysms. The inventors discovered robust calcification in human AAA samples, and detected osteoclast-like cells ("OLCs") in the medial (i.e., central) layer of the aneurismal aorta wall, though OLCs were barely detected in age-matched aortic tissues from autopsy both by TRAP staining, a conventional staining for osteoclast, and immunohistochemistry for the osteoclast marker, TRAP (see Example 1 and corresponding FIG. 1). The inventors further detected calcification and OLCs in experimental calcium chloride-induced AAA ($CaCl_2$ AAA) in mice.

Figure 2:
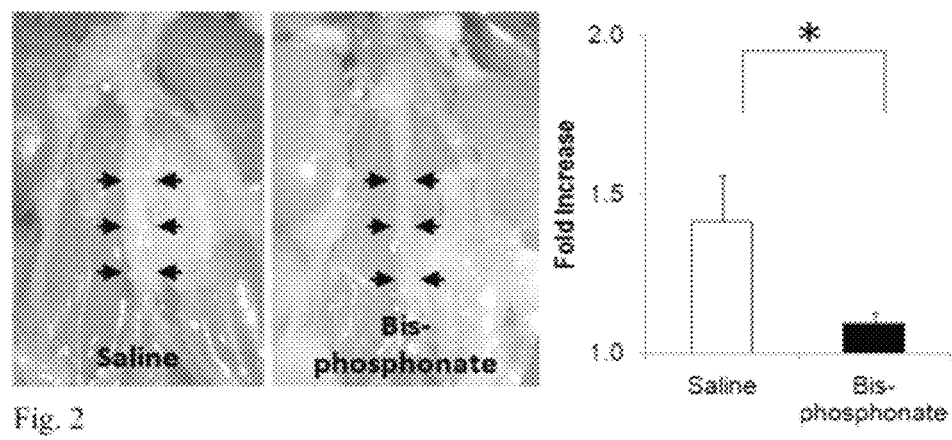
FIG. 2 illustrates the effect of OLCs inhibition on mouse AAA. Representative pictures of $CaCl_2$ AAA with intravenous ("i.v.") saline or bisphosphonate injection. Fold increase of the maximum size 7 days after the treatment was shown. n=3, P<0.05.

While no one mode of operation is adopted herein, the inventors hypothesized that overactivity of the osteoclast-like cells may induce the arterial damage that produces the aneurysm. Ultimately, by administering bisphosphonate at a dose equivalent to the doses used in human osteoporosis patients, the inventors showed complete inhibition of aneurysm formation in mice (see, e.g., Example 1 and corresponding FIG. 2).

At present, bisphosphonate has widely been accepted as a once weekly to once yearly, inexpensive treatment for osteoporosis. In view of the inventors' discoveries, the use of bisphosphonate could become a standard treatment to prevent or treat AAAs, which are usually treated by surgical intervention as described above, and for which no therapeutic drugs are known.

Accordingly, the present invention is directed to a method of treating aneurysms in blood vessels (vascular tissue), both to prevent their inception and growth, as well as to induce regression of established aneurysms. The invention extends not only to the prophylaxis, treatment, and management of aneurysms, as that term might be conventionally understood, but also to the prophylaxis, treatment, and management of any abnormal dilatations of blood vessels. Such dilatations are often considered to be predictive of aneurysm formation, or diagnostic of incipient aneurysms, and are treatable or preventable by means of the invention. Further, the method extends to the prophylaxis, treatment, and management of complications of atherosclerosis associated with aneurysms in arteries and other locations, including arterial occlusion (thrombosis), embolization, and dissection.

In one embodiment, the method of the invention involves administration of an anti-aneurysmal amount of a bisphosphonate compound to a subject in need of anti-aneurysmal therapy. An "anti-aneurysmal amount" of a bisphosphonate compound is an amount which prevents the formation of an aneurysm in a blood vessel, or which inhibits the progression or induces the regression of an established (pre-existing) aneurysm. Thus, a subject in need of anti-aneurysmal therapy is a subject which is vulnerable to the formation of an abnormal blood vessel dilatation or aneurysm, or a subject which exhibits an established blood vessel dilatation or aneurysm. The method of the invention is effective in resisting the formation of such aneurysms, and is helpful in causing the regression of pre-existing aneurysms to return the involved blood vessel (aneurysmal tissue) to a safer state, preferably to a normal or near normal state.

The method of this embodiment employs any suitable bisphosphonate compound having an anti-aneurysmal effect. A wide variety of bisphosphonate compounds are useful in the present method including, for example, etidronate, clodronate, tiludronate, pamidronate, neridronate, olpadronate, alendronate, ibandronate, risedronate, zoledronate, or a mixture thereof. In particular embodiments, the bisphosphonate is selected from non-nitrogen-containing bisphosphonate, and, in yet other methods, the bisphosphonate is a nitrogen-containing bisphosphonate. A preferred nitrogen-containing bisphosphonate is pamidronate, and a preferred non-nitrogen-containing bisphosphonate is etidronate.

Bisphosphonate compounds suitable for use according to the invention are commercially available or can be prepared by methods known in the art. In fact, a wide variety of such compounds are currently approved for unrelated drug therapies. Exemplary bisphosphonate compounds for use in the present invention include both non-N-containing bisphosphonates such as etidronate (commercially available as DIDRONEL), clodronate (BONEFOS, LORON), and tiludronate (SKELID), and N-containing bisphosphonates including pamidronate (APD, AREDIA), neridronate, olpadronate, alendronate (FOSAMAX), ibandronate (BONIVA), risedronate (ACTONEL), and zoledronate (ZOMETA, ACLASTA).

In another aspect, the invention provides a method for treating an aneurysm in vascular tissue of a subject which includes the step of administering an anti-aneurysmal amount of an anti-RANKL neutralizing antibody to a subject in need of anti-aneurysmal therapy, thereby inhibiting the development of, or inducing the regression of, an aneurysm in the vascular tissue of the subject.

The vascular tissue is preferably an artery of the subject, more preferably the aorta of the subject, namely the subject's abdominal aorta. Administration of the anti-RANKL neutralizing antibody is, e.g., via subcutaneous injection of the antibody to the subject.

In another aspect, the invention encompasses a method for inhibiting development of, or inducing regression of, an aneurysm in vascular tissue susceptible to the formation of, or exhibiting, an aneurysm. Such a method includes the step of contacting the vascular tissue with an anti-RANKL neutralizing antibody in an amount sufficient to inhibit development of, or induce regression of, an aneurysm in the vascular tissue.

Suitable anti-RANKL neutralizing antibodies for use in the invention are publically available. An exemplary antibody is Denosumab, which is a fully human monoclonal antibody useful for the treatment of osteoporosis, treatment induced bone loss, bone metastases, rheumatoid arthritis, multiple myeloma and giant cell tumor of bone. Denosumab is designed to target RANKL (RANK ligand), a protein that acts as the primary signal to promote bone removal. In many bone loss conditions, RANKL overwhelms the body's natural defense against bone destruction. Denosumab was developed by the company Amgen and was approved by U.S. Food and Drug Administration (FDA) for use in postmenopausal women with risk of osteoporosis in June 2010, under the trade name PROLIA, and for the prevention of skeletal-related events in patients with bone metastases from solid tumors in November 2010, as XGEVA, making it the first RANKL inhibitor to be approved by the FDA.

The maximal dosage of the active agent for a subject is the highest dosage that is effectively anti-aneurysmal, and that does not cause undesirable or intolerable side effects. The term "therapeutically effective amount", as it applies in the context of an anti-aneurysmal amount, is the amount of bisphosphonate compound sufficient to effect a treatment for aneurysm in a vascular tissue. In human subjects, an exemplary therapeutically effective amount of the bisphosphonate compound etidronate can be administered in a daily oral dosage of about 200 mg to about 400 mg, pamidronate in a monthly i.v. dosage of about 30 to about 90 mg, alendronate in a daily oral dosage of about 5 to about 10 mg daily or a weekly oral dosage of about 35 to about 70 mg, risedronate in a daily oral dosage of about 5 mg or a weekly oral dosage of about 35 mg, and zoledronate in a yearly dosage of about 5 mg.

Therapeutically effective dosages of anti-RANKL neutralizing antibody in the present methods of treating aneurysm ranges from about 1 mg to about 200 mg subcutaneous injection every four to six months, with 60 mg subcutaneous injection every six months a preferred dosage. Of course, the practitioner is guided by skill and knowledge in the field, and the present invention includes without limitation dosages which are effective to achieve the described phenomena.

The bisphosphonate compounds and antibodies useful according to the method of the invention exhibit their beneficial effect in a dose-dependent manner. For example, within broad limits, administration of larger quantities of a bisphosphonate compound or antibody will induce a larger or stronger response than will administration of a smaller amount. Moreover, anti-aneurysmal efficacy has been observed at dosages below the level at which toxicity is seen.

A bisphosphonate compound or antibody can be administered to a subject by any available and effective route, including enteral and parenteral routes. Injection of the agent, e.g., intravenous, intraarterial, intramuscular, subcutaneous, etc., can be employed as determined by the skilled artisan. Oral and intravenous administration are alternative preferred modes of administration. A suitable pharmaceutical composition for use in the method of the invention comprises a bisphosphonate compound or compound in a suitable pharmaceutical carrier or excipient as understood by practitioners in the art. The compositions are formulated with carriers suitable for administration orally, topically, by injection, or by other means. Time-release or controlled-delivery administration can be employed according to known methods. The means of delivery bisphosphonate compounds with the pharmaceutical carrier can be in the form of a capsule, compressed tablet, pill, solution, or suspension suitable for oral administration to the subject.

Bisphosphonate compounds and antibodies are particularly useful when formulated in the form of a pharmaceutical injectable dosage, including a bisphosphonate compound or antibody in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The chemical and physical characteristics of particular bisphosphonate compounds can influence the efficiency of particular modes of administration. For example, a more lipophilic compound could produce better blood levels by oral administration, but lower blood levels by subcutaneous injection, whereas another agent might have properties predisposing it to be more effectively delivered by vascular perfusion. The skilled artisan will understand how to effectively deal with such considerations as needed in the particular case.

The method of the invention can also be implemented by directed delivery of the bisphosphonate compound or antibody to the site of the incipient or existing aneurysm. In one embodiment, the invention involves the use of medical apparatus, such as an intravascularly implantable device, which enables intravascular delivery of the active agent. Implantable devices suitable for use include devices such as stents, catheters, embolic coils, filters, cannulas, protheses, and other such devices known in the art. The active agent can be included by coating onto a surface of the device, or if the device is made of polymeric material, the agent can be incorporated into the material for release into the surrounding tissue when implanted. Alternatively, the coating may include a polymeric material such as a water-soluble polymer, so that the active agent can be delivered in situ in a controlled release fashion. Polymers suitable for use in these methods are well known in the art, and include polymers such as cellulosic polymers, polyacrylates and polyacrylamides, polyvinyl alcohols, polyvinylpyrrolidone, and other hydrophilic polymers. Alternatively, polymers have porosity suited to release of the active agent into the surrounding tissues of fluids can be employed. In addition, catheters can be used to directly infuse or perfuse the agent into the blood vessel for controlled and localized or systemic delivery of the agent. A preferred mode of delivery the agent is to employ a stent with a coating of material for releasing the agent directly into the blood vessel wall at the site of implantation, while also providing direct structural support for the vessel at that site. Alternatively, a dual balloon perfusion catheter is used to isolate the site of dilatation or aneurysm, and the bisphosphonate compound can be delivered to the isolated area without involvement of surrounding tissues.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Recent studies have suggested calcification in arteriosclerosis is an organized and regulated process with many similarities to bone mineralization, which is regulated by osteoclast-like cells ("OLCs"). Bisphosphonate has previously been successfully used in clinics to treat osteoporosis by inhibiting osteoclast activity. In this example, the inventors demonstrate that the inhibition of OLCs with bisphosphonate leads to an inhibition of AAA development.

Initially, the inventors identified robust calcification in human AAA samples. The inventors have also identified the existence of OLCs in the medial layer of aneurismal aorta, which were barely detected in age matched aortic tissues from autopsy and stenotic disease both by tartrate-resistant acid phosphatase ("TRAP") staining, a conventional staining for osteoclast, and immunohistochemistry for osteoclast marker, TRAP (see FIG. 1). The inventors also have identified calcification and OLCs in experimental calcium chloride induced AAA ($CaCl_2$ AAA) in mouse. Finally, by administering pamidronate (1.25 mg/kg, i.v.), a nitrogen containing bisphosphonate, the inventors showed apparently complete inhibition of aneurysm formation in mice after 7 days. (see FIG. 2) The dose of pamidronate was equivalent to FDA approved dose of pamidronate for osteolytic bone lesions (90 mg/body).

Example 2

Figure 3A:
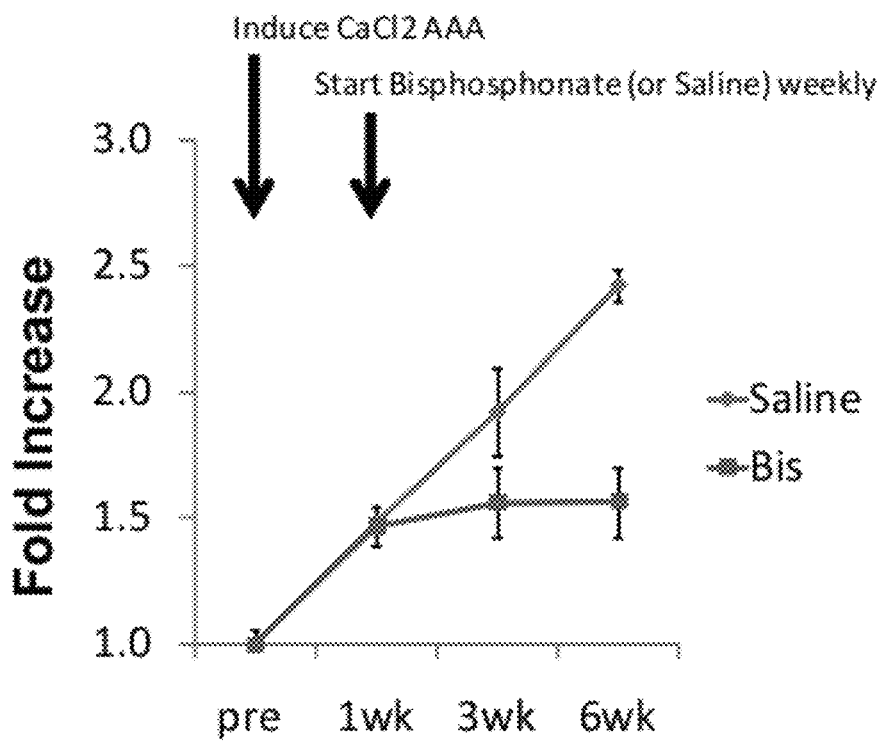
FIG. 3 shows the effect of bisphosphonate on developed aneurysm.
Figure 3B:
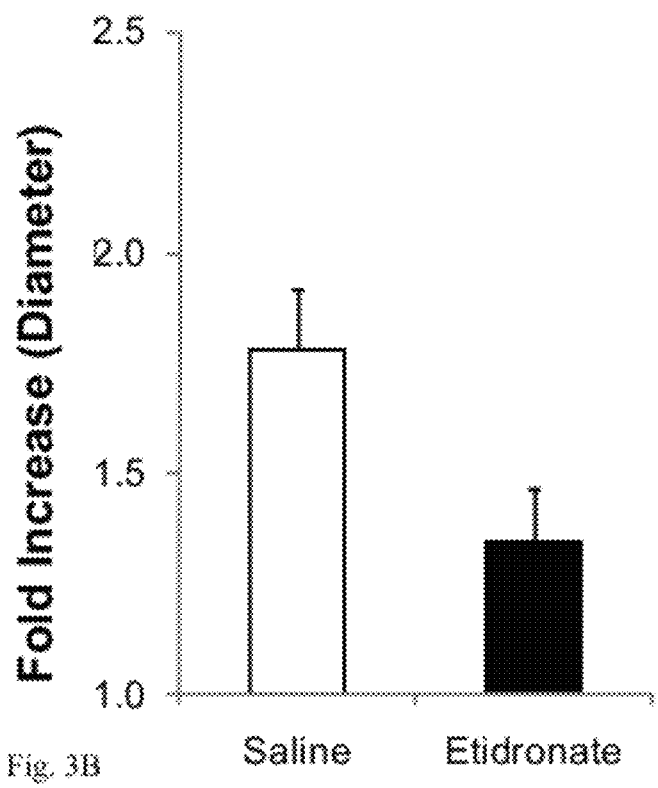

In this example, the inventors have tested the effect of the nitrogen-containing bisphosphonate compound pamidronate (Bis) on pre-existing (induced) AAAs in mice (over 5 weeks vs. control treatments; see FIG. 3A) by delaying the treatment until 7 days after aneurysm induction; treatment with weekly injection of bisphosphonate immediately halted further growth of the aneurysm whereas the aneurysms in the control animals (Saline) kept growing significantly larger. In addition, the inventors have extended their studies to cover the other major subclass of bisphosphonates (i.e., non-nitrogenous bisphosphonates) by studying the effect of etidronate (7.5 mg/kg i.v.) on aneurysm formation over 7 days (see FIG. 3B). The dose of etidronate was equivalent to FDA approved dose for Paget's disease (5-10 mg/kg).

Figure 4:
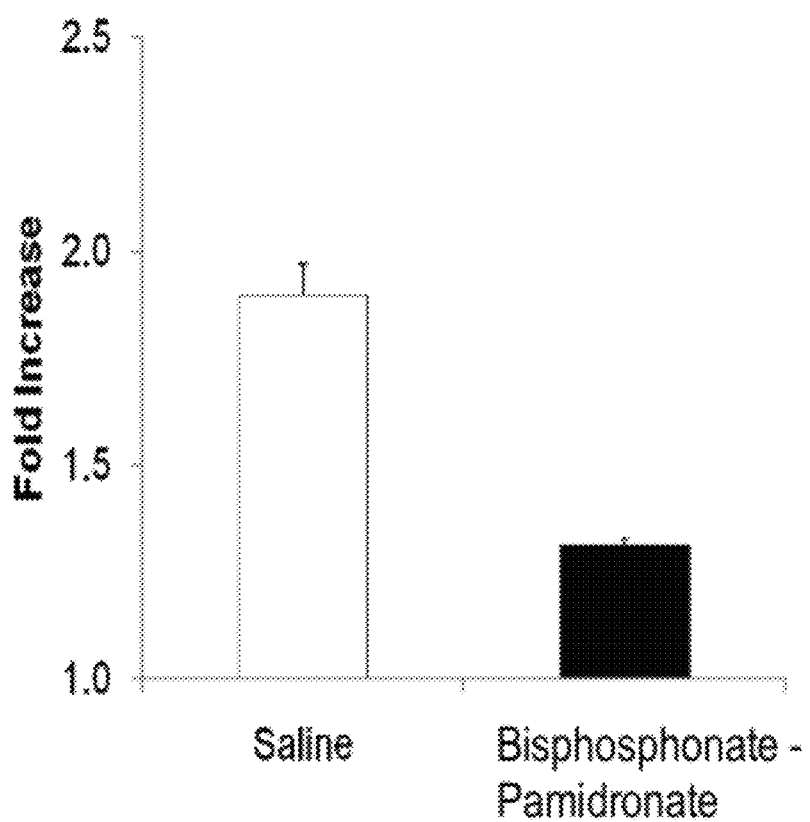
FIG. 4 illustrates bisphosphonate efficacy in treating AAA 6 weeks after AAA induction.
Figure 5:
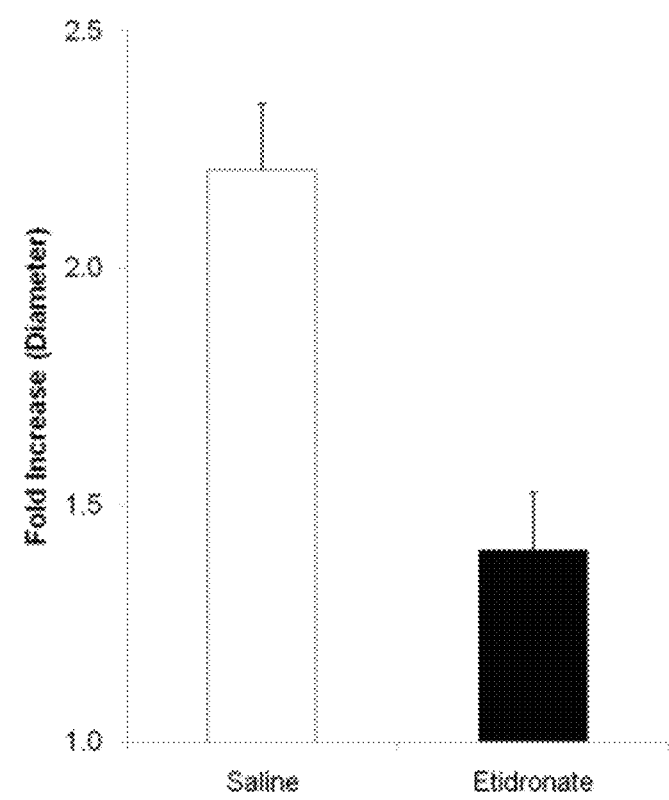
FIG. 5 shows $CaCl_2$-induced AAA and the effect of injected etidronate (approx. 7.5 mg/kg; i.v. administration) thereon. Saline injection acted as control. The animals were sacrificed 7 days post-injection.

In FIGS. 4 and 5, the inventors demonstrate the long term (6 weeks) effect of bisphosphonate on aneurysm formation by pamidronate and etidronate, respectively. The bisphosphonate treatment corresponding to the data in FIG. 3A was started 1 week post surgery. The bisphosphonate treatments resulting in the data shown in FIGS. 4 (pamidronate) and 5 (etidronate) differed from the previous treatment in that they included weekly bisphosphonate administration immediately after surgery through 6 weeks post surgery. In view of the present data, the inventors have demonstrated that the bisphosphonate family of chemicals is useful in the present methods for inhibiting both aneurysm formation and growth.

Example 3

Figure 6:
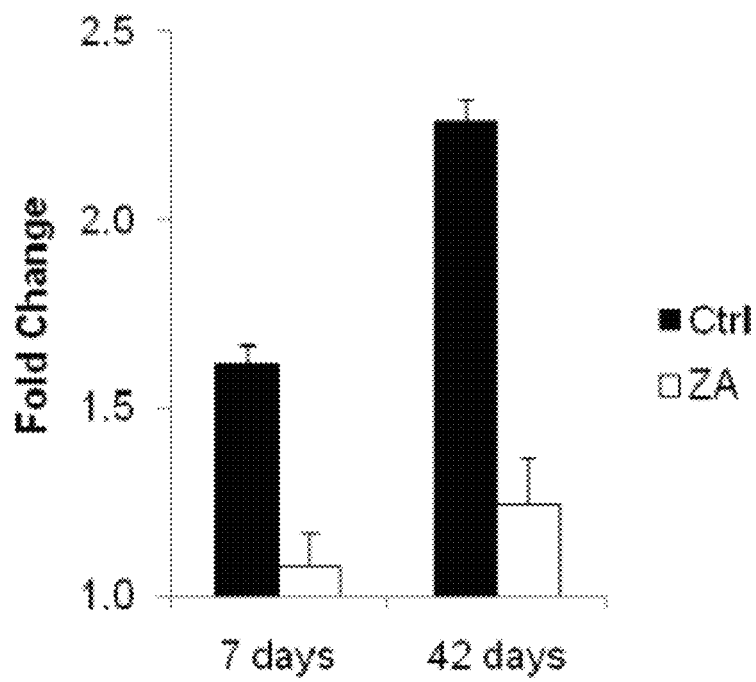
FIG. 6 shows data related to a Zoledronic acid (ZA) vs Normal Saline (Ctr) comparison.

In this example, the inventors have tested the short and long term effect of the newer generation of nitrogen-containing bisphosphonate compound zoledronate (ZA) (0.1 mg/kg, i.v. once) on AAAs. The dose of zoledronate was equivalent to FDA approved dose for osteoporosis and Paget's disease (5 mg/body, i.v. once). See FIG. 6.

Example 4

Figure 7:
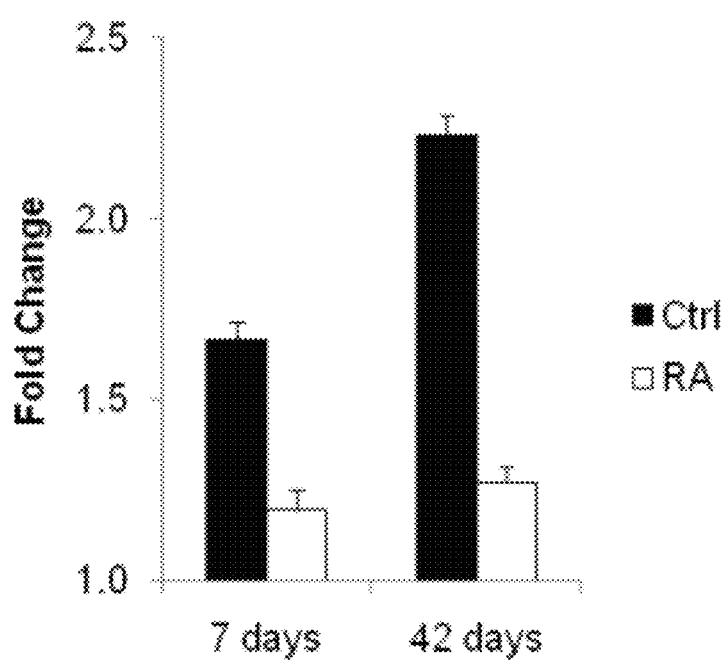
FIG. 7 depicts data related to neutralizing an antibody to RANKL (RA) vs Normal Goat IgG (Ctr) comparison.

In this example, the inventors have tested the short and long term effect of the neutralizing antibody of RANKL. This drug was proven to be effective for osteoporosis by inhibiting the differentiation of osteoporosis. The inventors demonstrate the short and long term effect of neutralizing antibody to RANKL (RA) (1.0 mg/kg, s.c. once) on aneurysm formation. The dose was equivalent to FDA approved dose for osteoporosis (60 mg/body, s.c. once). See FIG. 7.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

What is claimed is:

1. A method for treating an aneurysm in vascular tissue of a subject, comprising administering an anti-aneurysmal amount of a bisphosphonate compound to a subject in need of anti-aneurysmal therapy, thereby inhibiting the development of, or inducing the regression of, an aneurysm in the vascular tissue of said subject.

2. The method according to claim 1, wherein said vascular tissue is an artery of the subject.

3. The method according to claim 1, wherein said vascular tissue is the aorta of the subject.

4. The method according to claim 1, wherein said vascular tissue is the abdominal aorta of the subject.

5. The method according to claim 1, wherein said administering comprises intravenous injection of the bisphosphonate compound to the subject.

6. The method according to claim 1, wherein said administering comprises oral delivery of the bisphosphonate compound to the subject.

7. The method according to claim 1, wherein said bisphosphonate compound is etidronate, clodronate, tiludronate, pamidronate, neridronate, olpadronate, alendronate, ibandronate, risedronate, zoledronate, or a mixture thereof.

8. The method according to claim 1, wherein the bisphosphonate is a non-nitrogen-containing bisphosphonate.

9. The method according to claim 8, wherein the non-nitrogen-containing bisphosphonate is etidronate.

10. The method according to claim 1, wherein the bisphosphonate is a nitrogen-containing bisphosphonate.

11. The method according to claim 10, wherein the nitrogen-containing bisphosphonate is pamidronate.

12. A method for inhibiting development of, or inducing regression of, an aneurysm in vascular tissue susceptible to the formation of, or exhibiting, an aneurysm, comprising contacting said vascular tissue with a bisphosphonate compound in an amount sufficient to inhibit development of, or induce regression of, an aneurysm in said vascular tissue.

13. The method according to claim 12, wherein said bisphosphonate compound is etidronate, clodronate, tiludronate, pamidronate, neridronate, olpadronate, alendronate, ibandronate, risedronate, zoledronate, or a mixture thereof.

14. The method according to claim 12, wherein the bisphosphonate is a non-nitrogen-containing bisphosphonate.

15. The method according to claim 14, wherein the non-nitrogen-containing bisphosphonate is etidronate.

16. The method according to claim 12, wherein the bisphosphonate is a nitrogen-containing bisphosphonate.

17. The method according to claim 16, wherein the nitrogen-containing bisphosphonate is pamidronate.

18. The method according to claim 12, wherein said vascular tissue is arterial tissue.

19. The method according to claim 12, wherein said vascular tissue is aortic tissue.

20. The method according to claim 12, wherein said vascular tissue is abdominal aortic tissue.

21. The method according to claim 12, wherein said method comprises administering said bisphosphonate compound to a subject in an amount sufficient to inhibit development of, or induce regression of, an aneurysm in said subject.

* * * * *